United States Patent
Cox

(10) Patent No.: US 6,461,380 B1
(45) Date of Patent: *Oct. 8, 2002

(54) STENT CONFIGURATION

(75) Inventor: Daniel L. Cox, Palo Alto, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/124,376

(22) Filed: Jul. 28, 1998

(51) Int. Cl.⁷ ................................................. A61F 2/06
(52) U.S. Cl. ..................................... 623/1.17; 623/1.15
(58) Field of Search ........................... 623/1, 12, 1.15, 623/1.16, 1.17, 1.18; 606/108, 194, 195

(56) References Cited

U.S. PATENT DOCUMENTS

| | | | |
|---|---|---|---|
| 3,105,492 A | 10/1963 | Jeckel | |
| 3,657,744 A | 4/1972 | Ersek | |

(List continued on next page.)

FOREIGN PATENT DOCUMENTS

| | | |
|---|---|---|
| DE | 297 08879 U1 | 9/1997 |
| EP | 0 380 668 | 10/1988 |
| EP | 0 335 341 B | 10/1989 |
| EP | 0 338 816 A | 10/1989 |
| EP | 0 357 003 A2 | 3/1990 |
| EP | 0 361 192 A | 4/1990 |
| EP | 0 364 787 A1 | 4/1990 |
| EP | 0 372 789 A1 | 6/1990 |
| EP | 0 407 951 A | 1/1991 |
| EP | 0 421 729 A2 | 4/1991 |
| EP | 0 423 916 A1 | 4/1991 |
| EP | 0 428 479 A1 | 5/1991 |
| EP | 0 062 300 | 10/1992 |
| EP | 0 540 290 B1 | 10/1992 |
| EP | 0 517 075 | 12/1992 |
| EP | 0 541 443 A1 | 5/1993 |
| EP | 0 888 757 A1 | 1/1999 |
| FR | 2 677 872 | 12/1992 |
| FR | 2 758 253 | 7/1998 |
| GB | 2 070 490 A | 9/1981 |
| GB | 2 135 585 A | 9/1984 |
| GB | 0 221 570 A2 | 5/1987 |
| JP | 58-501458 | 9/1983 |
| JP | 62-231657 | 10/1987 |
| JP | 62-235496 | 10/1987 |
| JP | 63-214264 | 9/1988 |
| JP | 64-83685 | 3/1989 |
| JP | 1-299550 | 12/1989 |
| JP | 2-174859 | 7/1990 |

(List continued on next page.)

OTHER PUBLICATIONS

US 5,807,704, 9/1998, Richter (withdrawn)*
Dotter, Charlet T., Translumianlly Placed Coilspring Endarterial Tube Grafts, *Investigative Radiology*, pp. 329–332, Sep./Oct. 1969.

(List continued on next page.)

*Primary Examiner*—Bruce Snow
(74) *Attorney, Agent, or Firm*—Fulwider Patton Lee & Utecht, LLP

(57) ABSTRACT

A configuration for expandable stents herein a series of circumferentially disposed serpentine elements are linked to one another by bridging members that are connected to the serpentine elements at juncture points located along the straight linking segments between adjoining apexes. The bridging element is shaped such that during expansion of the stent, any longitudinal contraction within the serpentine element is compensated for by the deformation of the bridging member so as to maintain the overall length of the stent substantially constant.

6 Claims, 3 Drawing Sheets

U.S. PATENT DOCUMENTS

| | | | |
|---|---|---|---|
| 3,993,078 | A | 11/1976 | Bergentz'et al. |
| 4,130,904 | A | 12/1978 | Whalen |
| 4,140,126 | A | 2/1979 | Choudhury |
| 4,159,719 | A | 7/1979 | Haerr |
| 4,387,952 | A | 6/1983 | Slusher |
| 4,503,569 | A | 3/1985 | Dotter |
| 4,504,354 | A | 3/1985 | George et al. |
| 4,512,338 | A | 4/1985 | Balko et al. |
| 4,531,933 | A | 7/1985 | Norton et al. |
| 4,553,545 | A | 11/1985 | Maass et al. |
| 4,580,568 | A | 4/1986 | Gianturco |
| 4,619,246 | A | 10/1986 | Molgaard-Nielsen et al. |
| 4,649,922 | A | 3/1987 | Wiktor |
| 4,650,466 | A | 3/1987 | Luther |
| 4,655,771 | A | 4/1987 | Wallsten |
| 4,681,110 | A | 7/1987 | Wiktor |
| 4,706,671 | A | 11/1987 | Weinrib |
| 4,733,665 | A | 3/1988 | Palmaz |
| 4,739,762 | A | 4/1988 | Palmaz |
| 4,740,207 | A | 4/1988 | Kreamer |
| 4,762,128 | A | 8/1988 | Rosenbluth |
| 4,767,418 | A | 8/1988 | Deininger |
| 4,776,337 | A | 10/1988 | Palmaz |
| 4,795,458 | A | 1/1989 | Regan |
| 4,800,882 | A | 1/1989 | Gianturco |
| 4,830,003 | A | 5/1989 | Wolff et al. |
| 4,848,343 | A | 7/1989 | Wallsten et al. |
| 4,856,516 | A | 8/1989 | Hillstead |
| 4,870,966 | A | 10/1989 | Dellon et al. |
| 4,877,030 | A | 10/1989 | Beck et al. |
| 4,878,906 | A | 11/1989 | Lindemann et al. |
| 4,886,062 | A | 12/1989 | Wiktor |
| 4,892,539 | A | 1/1990 | Koch |
| 4,893,623 | A | 1/1990 | Rosenbluth |
| 4,907,336 | A | 3/1990 | Gianturco |
| 4,913,141 | A | 4/1990 | Hillstead |
| 4,922,905 | A | 5/1990 | Strecker |
| 4,943,346 | A | 7/1990 | Mattelin |
| 4,950,227 | A | 8/1990 | Savin et al. |
| 4,963,022 | A | 10/1990 | Sommargren |
| 4,969,458 | A | 11/1990 | Wiktor |
| 4,969,890 | A | 11/1990 | Sugita et al. |
| 4,986,831 | A | 1/1991 | King et al. |
| 4,990,155 | A | 2/1991 | Wilkoff |
| 4,994,071 | A | 2/1991 | MacGregor |
| 4,998,539 | A | 3/1991 | Delsanti |
| 5,002,560 | A | 3/1991 | Machold et al. |
| 5,007,926 | A | 4/1991 | Derbyshire |
| 5,015,253 | A | 5/1991 | MacGregor |
| 5,019,085 | A | 5/1991 | Hillstead |
| 5,019,090 | A | 5/1991 | Pinchuk |
| 5,026,377 | A | 6/1991 | Burton et al. |
| 5,034,001 | A | 7/1991 | Garrison et al. |
| 5,035,706 | A | 7/1991 | Gianturco et al. |
| 5,037,377 | A | 8/1991 | Alonso |
| 5,037,392 | A | 8/1991 | Hillstead |
| 5,037,427 | A | 8/1991 | Harada et al. |
| 5,041,126 | A | 8/1991 | Gianturco |
| 5,059,211 | A | 10/1991 | Stack et al. |
| 5,061,275 | A | 10/1991 | Wallsten et al. |
| 5,062,829 | A | 11/1991 | Pryor et al. |
| 5,064,435 | A | 11/1991 | Porter |
| 5,071,407 | A | 12/1991 | Termin et al. |
| 5,073,694 | A | 12/1991 | Tessier et al. |
| 5,078,720 | A | 1/1992 | Burton et al. |
| 5,078,726 | A | 1/1992 | Kreamer |
| 5,078,736 | A | 1/1992 | Behl |
| 5,084,065 | A | 1/1992 | Weldon et al. |
| 5,089,005 | A | 2/1992 | Harada |
| 5,089,006 | A | 2/1992 | Stiles |
| 5,092,877 | A | 3/1992 | Pinchuk |
| 5,100,429 | A | 3/1992 | Sinofsky et al. |
| 5,102,417 | A | 4/1992 | Palmaz |
| 5,104,404 | A | 4/1992 | Wolff |
| 5,108,416 | A | 4/1992 | Ryan et al. |
| 5,108,417 | A | 4/1992 | Sawyer |
| 5,116,318 | A | 5/1992 | Hillstead |
| 5,116,360 | A | 5/1992 | Pinchuk et al. |
| 5,116,365 | A | 5/1992 | Hillstead |
| 5,122,154 | A | 6/1992 | Rhodes |
| 5,123,917 | A | 6/1992 | Lee |
| 5,133,732 | A | 7/1992 | Wiktor |
| 5,135,536 | A | 8/1992 | Hillstead |
| 5,158,548 | A | 10/1992 | Cox |
| 5,161,547 | A | 11/1992 | Tower |
| 5,163,958 | A | 11/1992 | Pinchuk |
| 5,171,262 | A | 12/1992 | MacGregor |
| 5,180,368 | A | 1/1993 | Garrison |
| 5,183,085 | A | 2/1993 | Timmermans |
| 5,192,297 | A | 3/1993 | Hull |
| 5,192,307 | A | 3/1993 | Wall |
| 5,195,984 | A | 3/1993 | Schatz |
| 5,197,978 | A | 3/1993 | Hess |
| 5,222,971 | A | 6/1993 | Willard et al. |
| 5,226,913 | A | 7/1993 | Pinchuk |
| 5,234,456 | A | 8/1993 | Silverstrini |
| 5,242,452 | A | 9/1993 | Inoue |
| 5,282,823 | A | 2/1994 | Schwartz et al. |
| 5,282,824 | A | 2/1994 | Gianturco |
| 5,290,305 | A | 3/1994 | Inoue |
| 5,292,331 | A | 3/1994 | Boneau |
| 5,304,200 | A | 4/1994 | Spaulding |
| 5,314,444 | A | 5/1994 | Gianturco |
| 5,314,472 | A | 5/1994 | Fontaine |
| 5,330,500 | A | 7/1994 | Song |
| 5,356,433 | A | 10/1994 | Rowland et al. |
| 5,423,885 | A | 6/1995 | Williams |
| 5,449,373 | A | 9/1995 | Pinchasik et al. |
| 5,607,442 | A | 3/1997 | Fischell et al. |
| 5,632,771 | A | 5/1997 | Boatman et al. |
| 5,643,312 | A | 7/1997 | Fischell et al. |
| 5,669,932 | A | 9/1997 | Fischell et al. |
| 5,674,241 | A | 10/1997 | Bley et al. |
| 5,697,971 | A | 12/1997 | Fischell et al. |
| 5,707,386 | A | * 1/1998 | Schnepp-Pesch et al. ... 606/194 |
| 5,741,327 | A | * 4/1998 | Frantzen ........................ 623/1 |
| 5,755,781 | A | 5/1998 | Jayaraman |
| 5,776,161 | A | * 7/1998 | Globerman ................. 606/194 |
| 5,807,404 | A | 9/1998 | Richter |
| 5,810,872 | A | 9/1998 | Kanesaka et al. |
| 5,824,040 | A | 10/1998 | Cox et al. |
| 5,827,321 | A | 10/1998 | Roubin et al. |
| 5,836,964 | A | 11/1998 | Richter et al. |
| 5,843,120 | A | * 12/1998 | Israel et al. ................. 606/198 |
| 5,843,175 | A | 12/1998 | Frantzen |
| 5,853,419 | A | 12/1998 | Imran |
| 5,868,781 | A | 2/1999 | Killion |
| 5,868,783 | A | 2/1999 | Tower |
| 5,876,449 | A | * 3/1999 | Starck et al. ................. 623/12 |
| 5,879,370 | A | 3/1999 | Fischell et al. |
| 5,893,887 | A | 4/1999 | Jayaraman |
| 5,911,754 | A | * 6/1999 | Kanesaka et al. ............... 623/1 |
| 5,913,895 | A | 6/1999 | Burpee et al. |
| 5,922,005 | A | 7/1999 | Richter et al. |
| 5,922,020 | A | 7/1999 | Klein et al. |
| 5,925,061 | A | 7/1999 | Ogi et al. |
| 5,931,866 | A | 8/1999 | Frantzen |
| 5,935,162 | A | 8/1999 | Dang |
| 5,938,682 | A | 8/1999 | Hojeibane et al. |
| 5,938,697 | A | 8/1999 | Killion et al. |
| 5,948,016 | A | 9/1999 | Jang |

| | | | |
|---|---|---|---|
| 5,954,743 A | 9/1999 | Jang | |
| 5,964,798 A | 10/1999 | Imran | |
| 5,967,986 A | 10/1999 | Cimochowski et al. | |
| 5,968,093 A | 10/1999 | Kranz | |
| 5,980,552 A | 11/1999 | Pinchasik et al. | |
| 5,993,489 A | 11/1999 | Lewis et al. | |
| 6,001,125 A | 12/1999 | Golds et al. | |
| 6,004,348 A | 12/1999 | Banas et al. | |
| 6,013,091 A | 1/2000 | Ley et al. | |
| 6,017,365 A | 1/2000 | Von Oepen | |
| 6,019,789 A | 2/2000 | Dinh et al. | |
| 6,022,371 A | 2/2000 | Killion | |
| 6,022,374 A | 2/2000 | Imran | |
| 6,033,433 A * | 3/2000 | Ehr et al. | 623/1 |
| 6,033,435 A | 3/2000 | Penn et al. | |
| 6,039,755 A | 3/2000 | Edwin et al. | |
| 6,039,756 A | 3/2000 | Jang | |
| 6,042,597 A | 3/2000 | Kveen et al. | |
| 6,042,606 A | 3/2000 | Frantzen | |
| 6,048,361 A | 4/2000 | Von Oepen | |
| 6,051,020 A | 4/2000 | Goicoechea et al. | |
| 6,053,940 A | 4/2000 | Wijay | |
| 6,053,941 A | 4/2000 | Lindenberg et al. | |
| 6,053,943 A | 4/2000 | Edwin et al. | |
| 6,056,775 A | 5/2000 | Borghi et al. | |
| 6,056,776 A | 5/2000 | Lau et al. | |
| 6,059,822 A | 5/2000 | Kanesaka et al. | |
| 6,063,113 A | 5/2000 | Kavteladze et al. | |
| 6,066,168 A | 5/2000 | Lau et al. | |
| 6,066,169 A | 5/2000 | McGuinness | |
| 6,068,656 A | 5/2000 | Von Oepen | |
| 6,071,298 A | 6/2000 | Lashinski et al. | |
| 6,077,297 A | 6/2000 | Robinson et al. | |
| 6,080,191 A | 6/2000 | Summers | |
| 6,083,259 A | 7/2000 | Frantzen | |
| 6,086,604 A | 7/2000 | Fischell et al. | |
| 6,086,611 A | 7/2000 | Duffy et al. | |
| 6,090,127 A | 7/2000 | Globerman | |
| 6,093,199 A | 7/2000 | Brown et al. | |
| 6,093,203 A | 7/2000 | Uflacker | |
| 6,099,455 A | 8/2000 | Columbo et al. | |
| 6,099,559 A | 8/2000 | Nolting | |
| 6,099,560 A | 8/2000 | Penn et al. | |
| 6,099,561 A | 8/2000 | Alt | |
| 6,102,940 A | 8/2000 | Robichon et al. | |
| 6,106,548 A | 8/2000 | Roubin et al. | |
| 6,113,627 A | 9/2000 | Jang | |
| 6,113,628 A | 9/2000 | Borghi | |
| 6,123,721 A | 9/2000 | Jang | |
| 6,261,319 B1 * | 7/2001 | Kveen et al. | 623/1.15 |

FOREIGN PATENT DOCUMENTS

| | | |
|---|---|---|
| JP | 2-255157 | 10/1990 |
| JP | 3-9745 | 1/1991 |
| JP | 3-9746 | 1/1991 |
| JP | 3-151983 | 6/1991 |
| JP | 4-25755 | 2/1992 |
| WO | WO 91/07139 | 5/1991 |
| WO | WO 92/06734 | 4/1992 |
| WO | WO 92/09246 | 6/1992 |
| WO | WO 95/03010 | 2/1995 |
| WO | WO 96/03092 | 2/1996 |
| WO | WO 98/22159 | 5/1998 |
| WO | WO 98/48733 | 11/1998 |
| WO | WO 99/17680 | 4/1999 |

OTHER PUBLICATIONS

Rösch, J., M.D. et al., Transjugular Intrahepatic Portacaval Shunt: An Experimental Work, *The American Journal of Surgery* , pp. 588–592, vol. 121, May 1971.

Dotter, Charles T., Transluminal Expandable Nitinol Coil Stent Grafting: Preliminary Report, *Radiology Journal,* pp. 259–260, Apr. 1983.

Cragg, et al., Non–Surgical Placement of Arterial Endoprotheses: A New Technique Using Nitinol Wire, *Radiology Journal,* pp. 261–263, Apr. 1983.

Maass, et al., Radiological Follow–Up of Transluminally Inserted Vascular Endoprotheses: An Experimental Study Using Expanding Spirals, *Radiology Journal,* pp. 659–663, 1984.

$70^{th}$ Scientific Assembly and Annual Meeting: Scientific Program, *Radiology,* Washington, D.C., Nov. 25–30, 1984, Special Edition, vol. 153(P).

C.R. Bard, PE Plus Peripheral Balloon Dilation Catheter, *C.R. Bard, Inc.,* Aug. 1985.

Wright, et al., Percutaneous Endovascular Stents: an Experimental Evaluation, *Radiology Journal,* pp. 69–72, 1985.

Duprat, et al., Flexible Balloon–Expanded Stent for Small Vessels, *Radiology Journal,* pp. 276–278, 1987.

Charnsangavej, E., M.D., et al., Endovascular Stent of Use in Aortic Dissection: An In Vitro Experiment, *Radiology,* pp. 323–324, vol. 157, No. 2, Nov. 1985.

Palmaz, et al., Expandable Intraluminal Graft: A Preliminary Study, *Radiology Journal,* pp. 73–77, 1985.

$72^{nd}$ Scientific Assembly and Annual Meeting: RSNA Scientific Program, *Radiology,* Chicago: Nov. 30–Dec. 5, 1986, Special Edition, vol. 161(P).

Program: Day 2 (Nov. 18) The Radiological Society of North America, *Radiology,* Chicago: Nov. 30–Dec. 5, 1986, Special Edition, vol. 161(P).

Wallace, Michael J., et al., Tracheobronchial Tree: Expandable Metallic Stents Used in Experimental and Clinical Applications (Work in Progress), *Radiology* pp. 309–312, vol. 158, Feb. 1986.

Rösch, Josef, M.D., et al., Gianturco Expandable Wire Stents in the Treatment of Superior Vena Cava Syndrome Recurring After Maximum–Tolerance Radiation, *Cancer,* pp. 1243–1246, vol. 60, Sep. 1987.

Yoshioka, Tetsuya, et al., Self–Expanding Endovascular Graft: An Experimental Study in Dogs, *American Journal of Roentgeriology,* pp. 6730676, vol. 151, Oct. 1988.

Rösch, Josef, M.D., et al., Modified Gianturco Expandable Wire Stents in Experimental and Clinical Use, *Annales de Radiologie,* pp. 100–103, vol. 31, No. 2, 1988.

Mirich, David, et al., Percutaneously Placed Endovascular Grafts for Aortic Aneurysms: Feasibility Study, *Radiology,* pp. 1033–1037, 1989 Part 2.

Yoshioka, Tetsuya, et al., Development and Clinical application of Biliary Andoprothesis Using Expandable Metallic Stents, *Japan Radiological Society* pp. 1183–1185, vol. 48, No. 9 (with translation).

* cited by examiner

STENT CONFIGURATION

BACKGROUND OF THE INVENTION

The present invention generally relates to intravascular stents and more particularly pertains to improvements thereto that provide for enhanced longitudinal flexibility, increased longitudinal stability upon radial expansion and high strength.

Stents or expandable grafts are implanted in a variety of body lumens in an effort to maintain their patency. These devices are typically intraluminally implanted by use of a catheter which is inserted at an easily accessible location and then advanced to the deployment site. The stent is initially in a radially compressed or collapsed state to enable it to be maneuvered through the lumen. Once in position, the stent is deployed which, depending upon is configuration, is achieved either automatically or actively by for example, the inflation of a balloon about which the stent is carried on the catheter.

As stents are normally employed to hold open an otherwise blocked, constricted or occluded lumen, a stent must exhibit sufficient radial or hoop strength in its expanded state to effectively counter the anticipated forces. Not only is it advantageous to distribute such loads over as much of the stent as possible but it also is most beneficial to distribute the load over as much lumen wall as possible. As a consequence, it is desirable to maximize the coverage area of the stent in its expanded state. It is, however,. simultaneously necessary for the stent to be as small and compact as possible in its collapsed state in order to facilitate its advancement through the lumen. As a result, it is most advantageous for a stent to have as large an expansion ratio as possible.

An additional consideration is the longitudinal flexibility of the device. Such characteristic is important not only in maneuvering the stent into position, which may require the traversal of substantial convolutions of the vasculature, but also to better conform to any curvature of the vasculature at the deployment site. At the same time it is, however, necessary for the stent to nonetheless exhibit sufficient radial strength to provide the necessary support for the lumen walls upon deployment.

Another problem inherent in many prior art stent configurations is the longitudinal contraction that such structures typically undergo as they are radially expanded. This not only reduces the effective length of the stent in its deployed state but may cause abrasion trauma to be inflicted on the vessel walls during expansion.

A number of very different approaches have been previously devised in an effort to address these various requirements. A popular approach calls for the stent to be constructed wholly of wire. The wire is bent, woven and/or coiled to define a generally cylindrical structure in a configuration that has the ability to undergo radial expansion. The use of wire has a number of disadvantages associated therewith including for example, its substantially constant cross-section which may cause greater or lesser than an ideal amount of material to be concentrated at certain locations along the stent. Additionally, wire has limitations with respect to the shapes it can be formed into thus limiting the expansion ratio, coverage area, flexibility and strength that can ultimately be attained therewith.

As an alternative to wire-based structures, stents have been constructed from tube stock. By selectively removing material from such tubular starting material, a desired degree of flexibility and expandability can be imparted to the structure. Chemical etching techniques as well as laser-cutting processes are utilized to remove material from the tube. Laser cutting provides for a high degree of precision and accuracy with which very well defined patterns of material can be removed from the tube to conversely leave very precisely and accurately defined patterns of material in tact. The performance of such stent is very much a function of the pattern of material which remains. The selection of a particular pattern has a profound effect on the coverage area, expansion ratio and strength of the resulting stent as well as its longitudinal flexibility and longitudinal dimensional stability during expansion.

While the tube-based stents offer many advantages over the wire-based designs, it is nonetheless desirable to improve upon such designs in an effort to further enhance longitudinal flexibility and longitudinal dimensional stability during radial expansion without sacrificing radial hoop strength.

SUMMARY OF THE INVENTION

The present invention provides for an improved tube-based stent having enhanced longitudinal flexibility and longitudinal dimensional stability during radial expansion while exhibiting adequate hoop strength. The improvements arise with the selection of a precisely defined pattern of voids that are cut or etched into tube stock. The pattern of material that remains to define the stent comprises a series of generally parallel serpentine elements wherein such elements are interconnected to one another by advantageously shaped and positioned bridging members. More particularly, each serpentine element extends circumferentially about the stent such that successive apexes of each element alternatively extend distally and proximally along the stent's surface. The serpentine elements are successively spaced along the length of the stent and are oriented such that the pattern of apexes of each element is 180° out of phase relative to the pattern of apexes of each directly adjacent element. Each of the serpentine elements are joined to an adjacent element by at least one bridging member. The number, length and flexibility of such members determine the longitudinal flexibility of the resulting device in its collapsed as well as deployed state. The attachment of the bridging members to juncture points along the linking segments extending between the apexes causes the bridging members to distort during deployment. By matching the dimensional change imparted to the length of the stent caused by the expansion of each serpentine element to the dimensional change along the same direction caused by the rotation and distortion of the bridging element, the overall length of the stent is held constant during deployment. Additionally, the spacing of the juncture points away from the apexes distributes the stress that would otherwise be concentrated at such locations during expansion of the device.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

The present invention provides improved structural configurations for stents that serve to enhance the performance of such devices. Stents are introduced into the body and advanced through the vasculature to be expanded at a deployment site in an effort to maintain the patency of the vessel at such location. The stents of the present invention offer a high degree of longitudinal flexibility prior to and upon deployment and their overall lengths remain substantially constant during deployment so as to avoid traumatization of the vessel tissue during deployment. Moreover, the deployed stent provides sufficient radial hoop strength to enable it to withstand the loads imposed by the supported vessel.

The figures generally illustrate the invention and more particularly provide three preferred embodiments thereof. The stents are shown in their pre-expanded or collapsed state. In each case, the stent is shown in a longitudinally split and flattened condition in order to enhance clarity and aid in the understanding of its structure.

Figure 1:
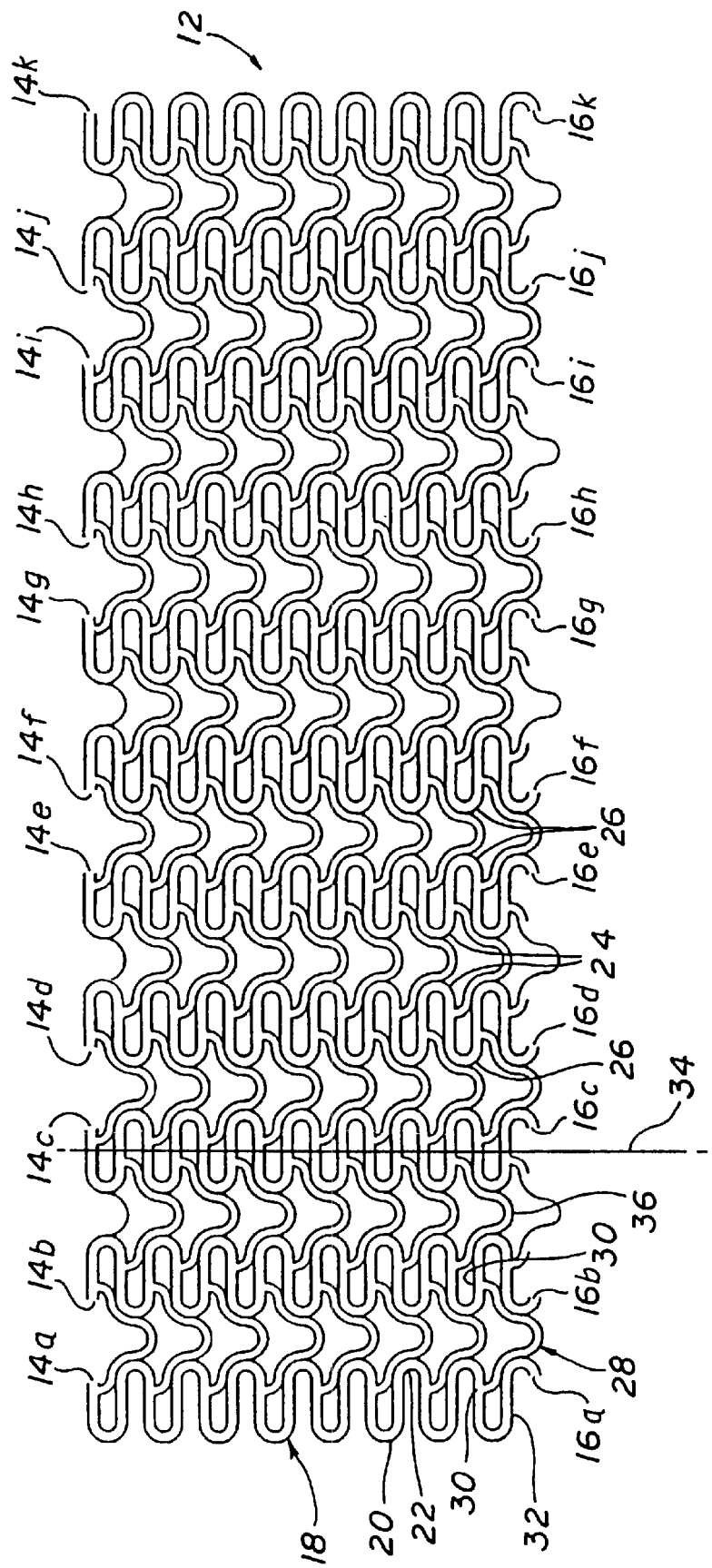
FIG. 1 is a flattened plan view of a section of stent of the present invention in its collapsed state.

FIG. 1 illustrates one of the preferred embodiments of the present invention. As indicated above, the stent 12 is shown in a longitudinally parted and flattened condition. In actuality, points 14a–k are joined to points 16a–k, respectively, to define a tubular structure. The stent consists of a plurality of serpentine elements 18 extending about the circumference of the stent. Each serpentine element has proximally extending apexes 20 and distally extending apexes 22 alternatingly arranged along its length. A plurality of such elements are assembled in parallel along the length of the stent wherein adjacent serpentine elements are arranged such that the respective patterns of apexes are 180° out of phase. Consequently, apexes of adjacent serpentine elements alternatingly face toward 24 one another and face away 26 from one another. Adjacent serpentine elements are joined to one another by bridging members 28. In the embodiment shown, a maximum number of bridging members, namely eight, are employed to join adjacent serpentine elements. A reduced number of such bridging members may be employed in order to increase the longitudinal flexibility of the stent, which is achieved primarily by freeing up serpentine elements 18 after removal of some bridging members. In other words, after a bridging member is removed, the corresponding serpentine element is unsupported and not constrained and can therefore expand and move more easily which in turn results in greater longitudinal flexibility.

Recurve portions 29, 31 of bridging members 28 of the present invention are each joined to adjacent serpentine elements at juncture points 30 positioned along the straight linking segments 32 extending between the apexes. Such points are positioned to not only avoid the highly stressed apex area but are also spaced apart from the centerline 34 of each serpentine element. More particularly, each bridging member is joined to the linking segment on the side of the centerline closest to the serpentine element being bridged by the bridging member. The bridging members are shaped such that the change in separation of its ends caused by the rotation and repositioning of such ends during deployment is offset by the change in length of the bridging member caused by its deformation such that a constant overall stent length is maintained. Additionally, the inclusion of a curved portion 36 near the center of each bridging member allows the bridging member to expand during stent expansion, which serves to enhance the flexibility of each bridging member and hence the flexibility of the stent.

During the stent's deployment, i.e., its expansion, by for example the inflation of a balloon positioned within the interior of the stent, each of the serpentine elements 18 becomes stretched to accommodate the increase in circumference. This is achieved by a bending of each apex 20, 22 wherein, instead of the 180° curves shown in FIG. 1, each apex assumes a curvature of something less than 180°, the actual magnitude thereof being dictated by the degree of stent expansion. As each apex bends, the linking portions 32 between apexes are caused to rotate, which forces the juncture points 30 to shift toward the centerline 34. The distortion of the bridging members 28 that results, namely, the opening up of the curved portion 36 results in a slight lengthening of the bridging member which precisely compensates for the increase in the spacing of opposed juncture points that results from the distortion each serpentine element undergoes as it becomes stretched. As a result, the overall length of the stent remains substantially unchanged as the stent undergoes expansion. A shifting of the stent relative the surrounding vessel walls is thereby avoided, obviating the infliction of trauma on the surrounding vessel tissue. Additionally, because each juncture point is spaced away from the apex, stresses are more independently distributed during deployment. Moving the juncture point away from the apex probably does not reduce the stress in and of itself. What it does is make the stresses of the apex more independent of those at the juncture. These stresses can then be more independently manipulated to reduce them individually as needed. Consequently, the stresses associated with the bending of the apex region and the stresses associated with the transfer of forces from the serpentine elements to the bridging members are separated from one another. By avoiding the concentration of stress, the stent is less prone to failure.

Figure 2:
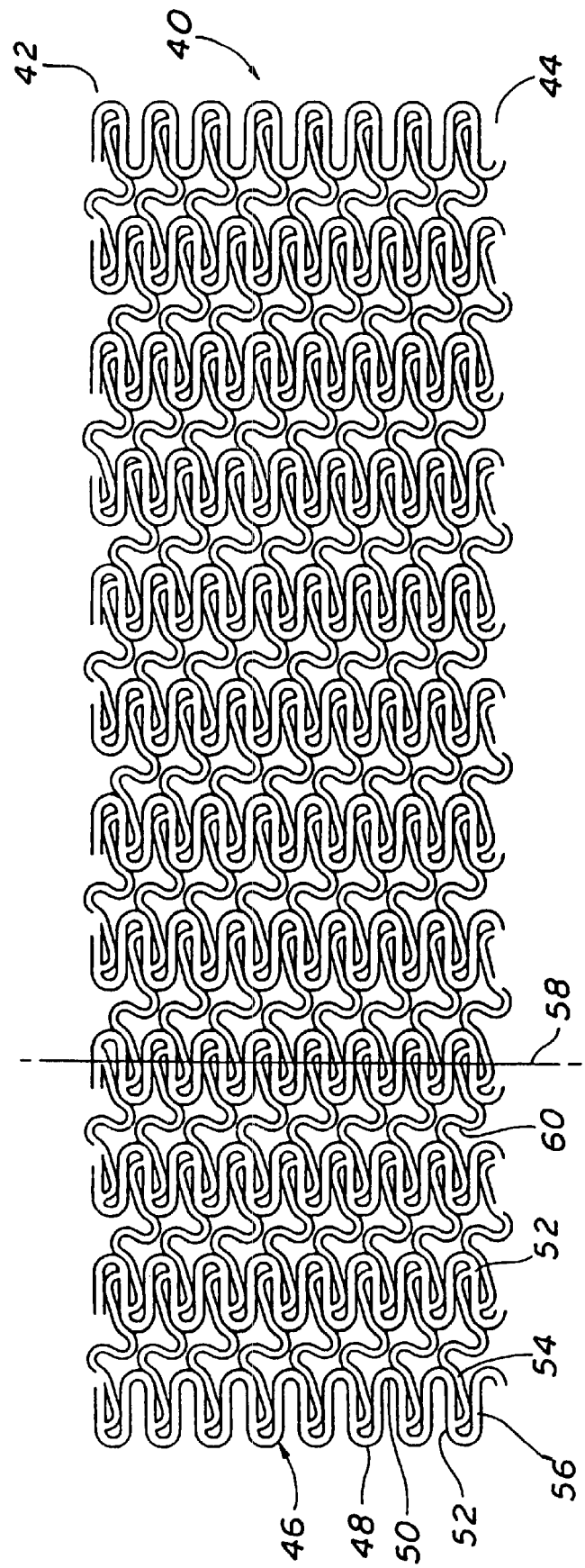
FIG. 2 is a flattened plan view of a section of an alternative embodiment stent in its collapsed state.

FIG. 2 illustrates an alternative embodiment stent of the invention. The tubular stent 40 is again shown in the parted and flattened state described above wherein all elements terminating along edge 42 are shown severed from the elements terminating along edge 44. Circumferentially extending serpentine elements 46 are arranged in parallel along the length of the stent. Each serpentine element has a series of proximal apexes 48 and distal apexes 50 alternatingly extending along the surface of the stent wherein each of the apexes are similarly shaped and dimensioned. Adjacent serpentine elements are arranged such that the respective patterns of apexes are 180° out of phase. The apexes of adjacent serpentine elements therefore alternatingly face toward one another and away from one another. The configuration and juncture points 52 of the bridging members 54 render this particular embodiment distinguishable from the embodiment illustrated in FIG. 1. More particularly, while each bridging member is joined to a linking segment 56 at a point set apart from the apex and the centerline 58, such juncture point is located on the side of the centerline facing away from the serpentine element which the bridging member interconnects. Consequently, the juncture points in this particular embodiment are set much further apart from one another than in the embodiment shown in FIG. 1. Similarly, it is thereby possible to accommodate a longer, bridging element in the stent configuration.

Each of the bridging members 54 includes a zig-zagging portion 60 near its center to not only provide enhanced length, but also to provide a configuration that will deform in a manner that compensates for the shift in position each juncture point undergoes during expansion. The total number of bridging members may be reduced from the eight shown thereby freeing up some distal apexes 50 and proximal apexes 48 which enhance the longitudinal flexibility of the stent both prior to and after deployment. As stated above, by removing a bridging member, corresponding serpentine elements are unsupported thereby primarily providing the increased flexibility in the stent.

During deployment, stent 40 performs similarly to the embodiment shown in FIG. 1, in that each serpentine element 46 stretches via the bending of its apexes 48, 50. As the stent expands and the linking segments 56 rotate, each of the juncture point 52 pairs are brought closer together. The forces inherent in such repositioning cause the bridging members 54, and more particularly the zig-zag portion 60 of the bridging member, to deform and elongate so as to maintain the overall length of the stent substantially constant.

Figure 3:
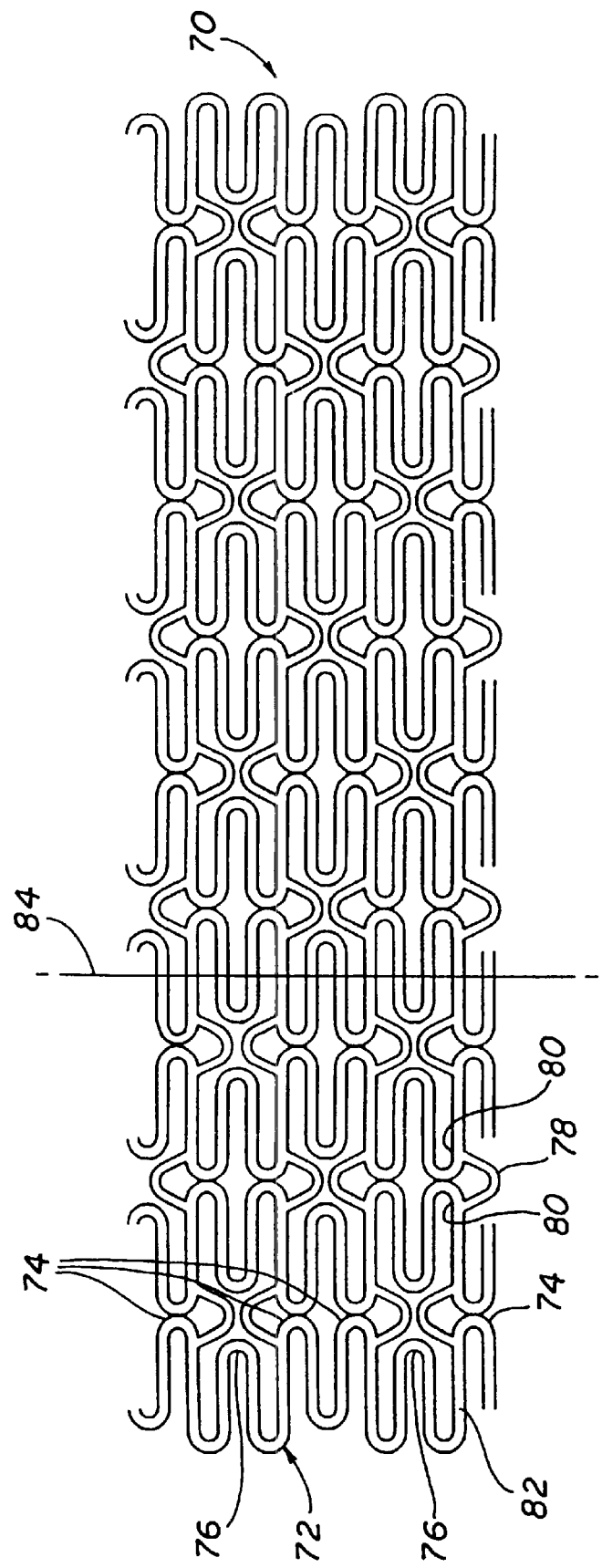
FIG. 3 is flattened plan view of a section of another alternative embodiment stent in it collapsed state.

FIG. 3 illustrates yet another embodiment of the present invention. Circumferentially extending serpentine elements 72 are again employed, but differ from those shown in FIGS. 1 and 2 in that the patterns defined along the distal and proximal edges of each serpentine element are irregular. In the embodiment shown, two sets of two maximally extended apexes 74 are separated by a single minimally extending apex 76 both on the proximal as well as distal edges of the serpentine element. Adjacent serpentine elements are again 180° out of phase and spaced such that the maximally extending apexes of adjacent serpentine elements preferably abut one another but do not necessarily have to abut. Each bridging member 78 is attached to a serpentine element at juncture points 80 located along the straight linking segment 82 and on the side of the centerline 84 closest to the serpentine segment bridged by the bridging member.

During deployment, the serpentine elements 72 become stretched causing the juncture points 80 to shift toward the centerline 84 and away from each other. The bridging members 78 become straightened thereby increasing in length to compensate for the dimensional change caused by the shifting of the juncture points. The overall length of the stent 70 thereby remains substantially constant at all times.

The stents of the present invention are preferably formed utilizing laser cutting techniques well known in the art and as disclosed in co-pending U.S. Ser. No. 08/783,565. The material used in the manufacture of such stents may be NiTi, stainless steel, tantalum, Pt/Ir, etc. After the appropriate shapes have been cut into the tube stock by the laser, the workpiece may be subjected to an electropolishing operation to provide a smoothly finished device.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. An expandable stent, comprising:

a series of circumferentially disposed serpentine elements, each such element including a series of U-shaped apexes alternatingly extending proximally and distally relative to a circumferentially extending centerline defined by each said element, successive apexes being joined by a substantially straight linking segment, said serpentine elements being arranged along said stent such that each series of apexes is 180 out of phase relative to the series of apexes of adjacent serpentine elements; and bridging members interconnecting adjacent serpentine elements, each bridging member including a pair of curvilinear leg portions joined together at their respective first ends by a U-shaped curved portion, the leg portions being symmetrically arranged relative to said U-shaped curved portion prior to expansion and the leg portions also having second ends, each second end joined to a different adjacent serpentine element at a juncture point located along said linking segment and offset from said centerline.

2. The stent of claim 1, wherein said bridging members are shaped to deform in such a way so as to compensate for any change in distance between juncture points interconnected by such bridging members that results from an expansion of the stent in order to maintain the overall length of the stent substantially constant.

3. The stent of claim 1, wherein the juncture points of each bridging members are located between the centerlines of the two serpentine elements interconnected by such bridging member.

4. The stent of claim 3, wherein said bridging member is shaped to increase in overall length during expansion of said stent in order to compensate for the increased separation of the juncture points.

5. The stent of claim 4, wherein said bridging member includes a U-shape.

6. The stent of claim 1, wherein said bridging elements interconnect all of said adjacent serpentine elements.

* * * * *